(12) United States Patent  
Amato

(10) Patent No.: US 8,282,635 B1
(45) Date of Patent: Oct. 9, 2012

(54) INTRA-ORAL DEVICES FOR CRANIOFACIAL SURGERY

(76) Inventor: Cyrus J. Amato, Califon, NJ (US)

( * ) Notice: Subject to any disclaimer, the term of this patent is extended or adjusted under 35 U.S.C. 154(b) by 1083 days.

(21) Appl. No.: 12/009,503

(22) Filed: Jan. 18, 2008

Related U.S. Application Data

(63) Continuation of application No. 12/004,542, filed on Dec. 20, 2007, now Pat. No. 7,909,610.

(60) Provisional application No. 60/885,570, filed on Jan. 18, 2007, provisional application No. 60/899,441, filed on Feb. 6, 2007.

(51) Int. Cl.
*A61B 17/00* (2006.01)
*A61B 17/58* (2006.01)
*A61C 3/00* (2006.01)

(52) U.S. Cl. .............. 606/57; 606/105; 433/18

(58) Field of Classification Search .............. 606/54–60, 606/71, 105; 433/18
See application file for complete search history.

(56) References Cited

U.S. PATENT DOCUMENTS

| | | | |
|---|---|---|---|
| 1,586,739 A | 2/1921 | Hanau | |
| 2,550,869 A * | 5/1951 | Salisbury | ............ 606/54 |
| 4,365,955 A | 12/1982 | Tradowsky | |
| 5,073,109 A | 12/1991 | El Hadary | |
| 5,172,695 A | 12/1992 | Cann et al. | |
| 5,201,736 A * | 4/1993 | Strauss | ............ 606/285 |
| 5,364,396 A * | 11/1994 | Robinson et al. | ............ 606/53 |
| 5,533,896 A | 7/1996 | Federici | |
| 5,682,886 A | 11/1997 | Delp et al. | |
| 5,720,612 A | 2/1998 | Shih | |
| 5,926,568 A | 7/1999 | Chaney et al. | |
| 6,096,079 A | 8/2000 | Eaton | |
| 6,112,109 A | 8/2000 | D'Urso | |
| 6,423,069 B1 | 7/2002 | Sellers | |
| 6,652,535 B2 | 11/2003 | Kvarnstrom et al. | |
| 6,701,174 B1 | 3/2004 | Krause et al. | |
| 6,908,469 B2 | 6/2005 | Sellers et al. | |
| 6,978,188 B1 | 12/2005 | Christensen | |
| 7,011,642 B2 | 3/2006 | Greene et al. | |
| 7,247,157 B2 | 7/2007 | Prager et al. | |
| 7,252,668 B2 | 8/2007 | Wolgen | |
| 2002/0040225 A1* | 4/2002 | Sellers et al. | ............ 606/105 |
| 2003/0097137 A1* | 5/2003 | Schendel | ............ 606/105 |
| 2004/0039259 A1 | 2/2004 | Krause et al. | |
| 2004/0097953 A1* | 5/2004 | Krenkel et al. | ............ 606/105 |

(Continued)

OTHER PUBLICATIONS

Cheung et al. "Vector Guidance Splint for Internal Maxillary Distraction." J. Oral Maxillofacial Surgery. 2007, pp. 1852-1856. American Association of Oral and Maxillofacial Surgeons.

(Continued)

*Primary Examiner* — Alvin Stewart
*Assistant Examiner* — Stuart S Bray
(74) *Attorney, Agent, or Firm* — Carella, Byrne, et al.; G. Glennon Troublefield; William Squire

(57) ABSTRACT

Intra-oral devices for distraction osteogenesis are described. Utilizing a medical model, bone-traced fixation plates with undercut portions are custom-fitted to the skeleton of the patient. To these plates rigid distraction platforms are connected. In the pre-surgical stage, skeletal segments are placed in the post-operative position and occlusal splints are constructed. The occlusal splints are modified to interengage the distraction platforms and to provide docking therefor. One or more distractors are mounted on the rigid platform and, upon operation thereof, guide the segment to the distraction endpoint. Optionally, after distraction and during consolidation, the distractors may be removed.

17 Claims, 8 Drawing Sheets

U.S. PATENT DOCUMENTS

| | | | |
|---|---|---|---|
| 2005/0085811 A1* | 4/2005 | Peckitt | 606/55 |
| 2005/0130092 A1* | 6/2005 | Minoretti et al. | 433/7 |
| 2006/0184168 A1* | 8/2006 | Posnick | 606/54 |
| 2007/0118243 A1 | 5/2007 | Schroeder et al. | |
| 2007/0293859 A1* | 12/2007 | Posnick | 606/57 |

OTHER PUBLICATIONS

Gulsen et al. "Maxillary Advancement with Internal Distraction Device in Cleft Palate Patients." J. Craniofacial Surgery. Jan. 2007, pp. 177-185.

Cheung et al. "Distraction of Le Fort II Osteotomy by Intraoral Distractor: A Case Report." J. Oral Maxillofacial Surgery, 64:856-860, 2006. American Association of Oral and Maxillofacial Surgeons.

Super et al. "A New Technique for Intraoral Maxillary Distraction: A Case Report." J. Oral Maxillofacial Surgery, 2006, pp. 536-542. American Association of Oral and Maxillofacial Surgeons.

Van Sickels et al. "The Use of Internal Maxillary Distraction for Maxillary Hypoplasia: A Preliminary Report." J. Oral Maxillofacial Surgery, 2006, pp. 1715-1720. American Association of Oral and Maxillofacial Surgeons.

Uckan et al. "Vector Alignment in Maxillary Distraction Osteogenesis." J. Craniofacial Surgery. 2006, 17:5, pp. 992-997.

Satoh et al. "Simultaneous Hybrid of Maxillary Le Fort I Halo Distraction and Mandibular Set-back for Patients with Severe Cleft Jaw Deformity." J. Craniofacial Surgery. 2006, 17:5, pp. 962-969.

Lauwers et al. "Maxillofacial Intraoral Distraction Osteogenesis Followed by Elastic Traction in Cleft Maxillary Deformity." Int. J. Oral Maxillofacial Surgery. 2005, 34:1, pp. 85-88. International Association of Oral and Maxillofacial Surgeons. Elsevier Ltd.

Suzuki et al. "Simple and Inexpensive Approach for the Management of Cleft Patients with the Twin-Track Distraction: Case Report." J Oral Maxillofacial Surgery. 2006, 64, pp. 722-726. American Association of Oral and Maxillofacial Surgeons.

Block et al. "Anterior Maxillary Advancement Using Tooth-Supported Distraction Osteogenesis." J Oral Maxillofacial Surgery. 1995, 53, pp. 561-565. American Association of Oral and Maxillofacial Surgeons.

Iannetti et al. "LeFort III Advancement with and without Osteogenesis Distraction." J Craniofacial Surgery. 2006, 17:3, pp. 536-543.

Polley et al. "Management of Severe Maxillary Deficiency in Childhood and Adolescence Through Distraction Osteogenesis with an External, Adjustable, Rigid Distraction Device." J Craniofacial Surgery. 1997, 8:3, pp. 181-185. Lippincott—Raven Publishers, USA.

Harada et al. "Long-term Maxillomandibular Skeletal and Dental Changes in Children with Cleft Lip and Palate After Maxillary Distraction." Oral Surgery, Oral Medicine, Oral Pathology, Oral Radiology, and Endodontics (OOOE). 2006, 102, pp. 292-299. Mosby, Inc.

Huang et al. "Long-term Follow-up after Maxillary Distraction Osteogenesis in Growing Children with Cleft Lip and Palate." Cleft Palate—Craniofacial J. 2007, 44:3, pp. 274-277.

Minami et al. "Maxillary Distraction Osteogenesis in Cleft Lip and Palate Patients with Skeletal Anchorage." Cleft Palate—Craniofacial J. 2007, 44:2, pp. 137-141.

Baker et al. "Rapid Maxillary Distraction Protocol Utilizing the Halo Distraction System and Rigid Internal Fixation." Cleft Palate—Craniofacial J. 2007, 44:5, pp. 476-481.

Kragskov et al. "Comparison of the Reliability of Craniofacial Anatomic Landmarks Based on Cephalometric Radiographs and Three-Dimensional CT Scans." Cleft Palate—Craniofacial J. 1997, 34:2, pp. 111-116.

Schroeder, James R. "Advanced Manufacturing Technology Changes the Way Implants are Designed and Produced." BONEZone. Fall 2006.

McAllister et al. "Bone Augmentation Techniques" [Review]. J Periodontology. Mar. 2007, 78:3, pp. 377-396.

Esposito et al. "The Efficacy of Various Bone Augmentation Procedures for Dental Implants: a Cochrane Systematic Review of Randomized Controlled Clinical Trials" [Review]. Intl. J. Oral Maxillofacial Implants. 2006, 21:5, pp. 696-710.

Chanchareonsook et al. "The Effect of Cranio-Maxillofacial Osteomies and Distraction Osteogenesis on Speech and Velopharyngeal Status: A Critical Review." [Review]. Cleft Palate—Craniofacial J. 2006, 43:4, pp. 477-487.

Koudstaal et al. "Surgically Assisted Rapid Maxillary Expansion (SARME): A Review of the Literature" [Review]. Intl. J Oral Maxillofacial Surgery. 2005, 34:7, pp. 709-714.

Barry et al. "Maxillary Alveolar Ridge Augmentation Using Distraction Osteogenesis: A Literature Review and Case Report" [Review]. J Irish Dental Association. 2005, 51:2, pp. 63-67.

Zadeh, Homayoun H. "Implant Site Development: Clinical Realities of Today and the Prospects of Tissue Engineering" [Review]. J California Dental Association. 2004, 32:12, pp. 1011-1020.

Figueroa et al. "Long-term Skeletal Stability after Maxillary Advancement with Distraction Osteogenesis Using a Rigid External Distraction Device in Cleft Maxillary Deformities" [Review]. Plastic and Reconstructive Surgery. 2004, 114:6, pp. 1382-1392, discussion pp. 1393-1394.

Oikarinen et al. "Augmentation of the Narrow Traumatized Anterior Alveolar Ridge to Facilitate Dental Implant Placement" [Review]. Dental Traumatology. 2003, 19:1, pp. 19-29.

Lo et al. "Blindness as a Complication of Le Fort I Osteotomy for Maxillary Distraction" [Review]. Plastic and Reconstructive Surgery. 2002, 109:2, pp. 688-698, discussion 699-700.

Sinn et al. "Stereolithography for Craniofacial Surgery." J Craniofacial Surgerry. 2006, 17:5, pp. 869-875.

Wang et al. "The Inter-relationship Between Mandibular Autorotation and Maxillary LeFort I Impaction Osteotomies." J Craniofacial Surgerry. 2006, 17:5, pp. 898-904.

Ellis, Edward. "Accuracy of Model Surgery: Evaluation of an Old Technique and Introduction of a New One." J Oral Maxillofacial Surgery. 1990, 41, pp. 1161-1167. American Association of Oral and Maxillofacial Surgeons.

Ellis, Edward. "Bimaxillary Surgery Using an Intermediate Splint to Position the Maxilla." J Oral Maxillofacial Surgery. 1999, 57, pp. 53-56. American Association of Oral and Maxillofacial Surgeons.

Ellis et al. "Accuracy of Face-bow Transfer: Effect on Surgical Prediction and Postsurgical Result." c.

Gil et al. "Predictability of Maxillary Repositioning During Bimaxillary Surgery: Accuracy of a New Technique." Int. J. Oral Maxillofacial Surgery. 2007, 36, pp. 296-300. Interational Association of Oral and Maxillofacial Surgeons. Elsevier Ltd.

Kunz et al. "Theoretical Considerations for the Surgical Correction of Mandibular Deformity in Hemifacial Microsomia Patients Using Multifocal Distraction Osteogenesis." J Oral Maxillofacial Surgery. 2003, 61, pp. 364-368. American Association of Oral and Maxillofacial Surgeons.

Wagener et al. "Management of Infants with Pierre Robin Sequence." Cleft Palate-Craniofacial J. 2003, 40:2, pp. 180-185.

McCarthy et al. "Molding of the Regenerate in Mandibular Distraction: Clinical Experience." Plastic and Reconstructive Surgery. 2003, 112, pp. 1239-1246. American Society of Plastic Surgeons.

Huisinga-Fischer et al. "Longitudinal Results of Mandibular Distraction Osteogenesis in Hemifacial Microsomia." J Craniofacial Surgery. 2003, 14:6, pp. 924-933.

Sant'anna et al. "Histological Evaluation of the Temporomandibular Joint After Bilateral Vertical Ramus Mandibular Distraction in a Canine Model." J Craniofacial Surgery. 2007, 18:1, pp. 155-162.

Freitas et al. "Mandible Distraction Using Internal Device: Mathematical Analysis of the Results." J Craniofacial Surgery. 2007, 18:1, pp. 29-38.

Sayan et al. "Two-stage Treatment of TMJ Ankylosis by Early Surgical Approach and Distraction Osteogenesis." J Craniofacial Surgery. 2007, 18:1, pp. 212-217.

Nadjmi et al. "Trans-sinusal Maxillary Distraction for Correction of Midfacial Hypoplasia: Long-term Clinical Results." Intl. J. Oral Maxillofacial Surgery. 2006, 35:10, pp. 885-896.

Suzuki et al. "New Fixation method for Maxillary Distraction Osteogenesis Using Locking Attachments." J Oral Maxillofacial Surgery. 2006, 64:10, pp. 1553-1560.

Liou, Eric Jein-Wein. "Effective Maxillary Orthopedic Protraction for Growing Class III Patients: a Clinical Application Simulates Distraction Osteogenesis." Progress in Orthodontics. 2005, 6:2, pp. 154-171.

Rachmiel et al. "Long-term Results in Maxillary Deficiency Using Intraoral Devices." Intl. J. Oral Maxillofacial Surgery. 2005, 34:5, pp. 473-479.

Gurgan et al. "Alterations in Gingival Dimensions Following Rapid Canine Retraction Using Dentoalveolar Distraction Osteogenesis." European J. Orthodontics. 2005, 27:4, pp. 324-332.

Sassano et al. "Intraoral Distraction of a Patient With Premaxilla Agenesis." J. Craniofacial Surgery. 2005, 16:3, pp. 500-504.

Stryker Leibinger. "DynaForm Intraoral Distraction System." Product Catalogue, 2002.

Synthes Maxillofacial. "The Maxillar Distractor System." Product Catalogue, 2002.

KLS Martin, L.P. "Distraction Product Catalogue." Undated.

Oral Osteodistraction, L.P. "Redefining the Future of Maxillo-Facial Surgery." Product Literature. Undated.

* cited by examiner

INTRA-ORAL DEVICES FOR CRANIOFACIAL SURGERY

CROSS REFERENCE TO RELATED APPLICATIONS

This is a Continuation-in-Part of application Ser. No. 12/004,542 filed Dec. 20, 2007 entitled Computer-Aided System of Orthopedic Surgery and, further, this Application is a non-provisional of Provisional Application 60/885,570 filed Jan. 18, 2007 entitled Craniofacial Maxillary Custom Intra-Oral Distraction Device and of Provisional Application 60/899,441 filed Feb. 6, 2007, entitled Intra-Oral Mandibular Distraction Device, said applications are incorporated herein by reference.

BACKGROUND OF THE INVENTION

1. Field of Invention

The present invention relates to intra-oral devices for craniofacial distraction osteogenesis, and, more particularly, to an intra-oral system for both maxillary and mandibular distraction osteogenesis. The system uses computer generated, for example computed tomography (CT), information to form custom-cast, bone-traced appliances so as to attain especially strong connections to the facial bones. Stabilized platforms are attached thereto for controlling the distribution of distraction forces. Further, the CT data is used, either in the form of a medical model or a visual imaging process, to create an occlusal splint, the distractor mounting arrangement and distractor guides to manage the distraction osteogenesis endpoint. The intra-oral devices hereof overcome the vector sensitivity and distraction force dissipation of prior devices and are omnidirectional distraction devices.

2. Description of the Related Art

In the past, computerization for surgical preplanning purposes has provided stereolithographic models of the anatomic site. These are three-dimensional models constructed using digitized information from scanning devices such as laser and acoustic reflection apparatus and various types of transmission apparatus including X-ray, magnetic resonance imaging (MRI), positron emission (PET or SPECT) as well as ultrasonic radiation.

Upon data being captured by scanning a series of spaced parallel planes, the scans are combinable by computed-tomographic (CT) techniques to construct a three dimensional projection of the scan in the form of a medical model such as a stereolithographic representation. Anatomical modeling using CT-scan data is well known and is widely accepted in pre-operative planning, rehearsal of surgical procedures, and the manufacture of prosthetic devices.

U.S. Pat. No. 6,112,109 of D'urso and U.S. Patent Application Publication 2005/0133955 both describe the use of CT-scan data for constructing prosthetic devices that are custom-fit to provide a better relationship between the remaining healthy bone and the orthopedic implant.

To implement the inventor's system of orthopedic surgery several heretofore unknown devices needed to be developed. A craniofacial anatomic surgical simulator is described, infra, for mounting and working the stereolithographic model. As background to this development, Krause et al. in U.S. Pat. No. 6,701,174 comment that in the complex area of bone distraction surgery "it is difficult, if not impossible, to make accurate surgical plans based solely on a limited number of two-dimensional renderings of bone geometry. This is because of the complex and inherently three-dimensional nature of bone deformities as well as of fixator geometry. Furthermore, two-dimensional depictions of surgical plans may not accurately portray the complexities involved in accessing the target positions of the osteotome and fixator pins surrounding the operated bone. Lack of three-dimensional modeling of these geometric complexities makes it difficult to accurately mount the fixator on the patient according to the presurgical plan".

The computer-assisted preplanning of Krause et al. made an early attempt to resolve this long-felt need through the use of a Taylor Spatial Frame—a collection of fixator struts and associated software; however, they found that the apparatus did not provide visual feedback on how the fixator frame and bone fragments should be moved over time.

As further background to the surgical simulator hereof, in the medical literature Cheung et al. In a 2007 article entitled, *Vector Guidance Splint for Internal Maxillary Distraction* (*JL Oral Maxillofacial Surgery*, pp. 1852 et seq.) reports using a Hanau Engineering Articulator, developed in the 1920's.

Taking dental articulators as the forebears of the Craniofacial Anatomic Surgical Simulator hereof leads one to view the articulator patent art starting with Hanau, U.S. Pat. No. 1,586,739 and leading patents to Tradowsky, U.S. Pat. No. 4,365,955; El Hadary, U.S. Pat. No. 5,073,109; Federici, U.S. Pat. No. 5,533,896; and Shih, U.S. Pat. No. 5,720,612. None of these devices fulfill the simulation requirements of the disclosure at hand.

The prior art for distraction osteogenesis relates back to the Ilazarov procedure in which bones were separated at an osteotomy site into two segments and gradually further separated until the new growth at the void reached the required expansion. Mechanical aids supporting the process became known as distractors and were usually screw-driven devices with each turn being translatable into an additional incremental separation. Initially, maxillofacial and mandibular distractions were performed using external frames and such frames are still in use, typically the R.E.D. II System (KLS-Martin Rigid External Distraction System, KLS Martin L. P., Jacksonville, Fla. 32250).

Later, Guerraro, U.S. Pat. No. 5,895,387 and Samchukov, U.S. Pat. No. 5,980,252 described intra-oral devices for jaw lengthening and alveolar distraction; however, the applications thereof do not include the stabilization or the maintenance of the stomatognathic system described herein.

In the intra-oral devices herein, through the use of advanced techniques enabled by computed tomographic information, by computer-aided surgical simulation, and by medical models, the surgeon is able to provide omnidirectional distraction osteogenesis with pre-established endpoints.

SUMMARY

In the parent case, a craniofacial anatomic surgical simulator (CASS) for mounting a medical model is described. The CASS provides a mounting arrangement for a modified (truncated) stereolithographic model which includes a craniomaxillary portion, a mandibular portion and a simulated temporomandibular joint. The CASS facilitates the structuring of pre-operative intra-oral devices required for omnidirectional distraction osteogenesis. The intra-oral system for both maxillofacial and mandibular distraction osteogenesis are described herein.

The intra-oral system descriptions may be simplified by the following unifying analysis. First, the skeletal anchoring is of major importance. In both cases, anchoring is achieved with custom-fitted, bone-traced components which further utilize mechanical undercuts to ensure rigid stabilization. Then, serving the dual purpose of segment stability during distraction and maintenance of the stomatognathic system during distraction and consolidation, a rigid cross-arch, intra-oral framework structurally depending from the anchoring components is built. Using the medical model, the surgery is simulated and the mobile segment is placed in the post-operative position to predetermine the endpoint of the distraction and to form a distraction splint. A fixed, precision docking component is then structured that includes a negative-image impression of the distraction splint secured to the mobile segment. Guide wires and other guide means are used during the distraction process to ensure that the distraction trajectory is maintained on the designed course and that the distraction reaches the predetermined, precise endpoint.

The description of the preferred embodiments, infra, describes two basic intra-oral devices. The intra oral device for maxillofacial distraction osteogenesis includes a pair of anatomically contoured fixation plates which are cast from wax imprints formed on the stereolithographic reproduction of the malar bone. The fixation plates are each extended and at the posterior end is wrapped about or undercuts the malar bone and, further at the anterior end, is wrapped about or undercuts the piriform rim. Between the exact replicating of the computer generated surface and bone configuration at the extremities, the plate is designed for efficient emplacement thereof during surgery and is secured by strategically placed bone screws. Because the distraction plate device is cast to the stereolithographic model, no bending of the appliance or other fitting steps are required at the time of emplacement.

Besides the contoured distraction plate just described, the maxillofacial intra-oral device further includes a stabilized platform formed by a docking bar and connecting rods. The connecting rods extend between the fixation plates and a docking bar, and an occlusal splint. In the pre-distraction position, the docking bar and the occlusal splint are spaced apart. After distraction, the edge of the docking bar and that of the occlusal splint nest one within the other in a final post-operative location. The path of movement from initial to final position is one in which continuous correction takes place and in effect is omnidirectional and independent from a specific vector alignment

OBJECTS AND FEATURES OF THE INVENTION

It is an object of the present invention to utilize simulation information gained from a computer-aided system of surgery to construct intra-oral devices that are designed in accord with anatomic variables, including the contour and surface mapping of the bone, the quality of the bone, and the location of neurovascular and other relevant anatomic structures.

It is another object of the present invention to provide for prefitted, custom fabricated intra-oral devices for omnidirectional distraction osteogenesis, including devices for craniofacial surgery, intra-oral distractors, docking bars, and modified occlusal splints.

It is yet another object of the present invention to provide an anatomically contoured fixation plate crafted on the stereolithographic model.

It is a feature of the present invention that the mandibular intra-oral device hereof maintains the stomatognathic system and the physiological functioning of the patient throughout the distraction osteogenesis treatment.

It is another feature of the present invention that the distraction osteogenesis thereof is performed from rigid intra-oral structures securely mounted to anchoring bones of the skeleton of the patient.

It is yet another feature of the present invention that the endpoint of the distraction osteogenesis hereof is predetermined and controlled by docking of the movable segment.

It is still yet another feature of the present invention that the interaction of the rigid structures and the modified occlusal splints hereof result in omnidirectional distraction osteogenesis.

Other objects and features of the present invention will become apparent from a review of the following detailed description thereof.

BRIEF DESCRIPTION OF THE DRAWINGS

The invention is described in more detail below with reference to the embodiments shown in the drawing in which like elements are labeled similarly.

In the drawings which follow, the same parts in the various views are provided the same reference designators.

FIGS. 9A and 9B are cross-sectional views wherein FIG. 9A shows the relationship between the contoured fixation plate and the malar bone and FIG. 9B shows the relationship between the docking bar and the occlusal splint; and, FIG. 10 is a perspective view of the intra-oral device of this invention for mandibular omnidirectional distraction osteogenesis;

DESCRIPTION OF THE PREFERRED EMBODIMENTS

This disclosure describes a new system of orthopedic surgery, which changes present-day craniofacial procedures and is particularly applicable to distraction osteogenesis. In order to work within this new surgical milieu, an initial trio of inventions were required. While the following introductory discussion uses distraction osteogenesis as exemplary, it should be borne in mind that certain devices, such as the craniofacial anatomic surgical simulator (CASS), may be more broadly applied.

Surgical Preplanning

Figure 1:
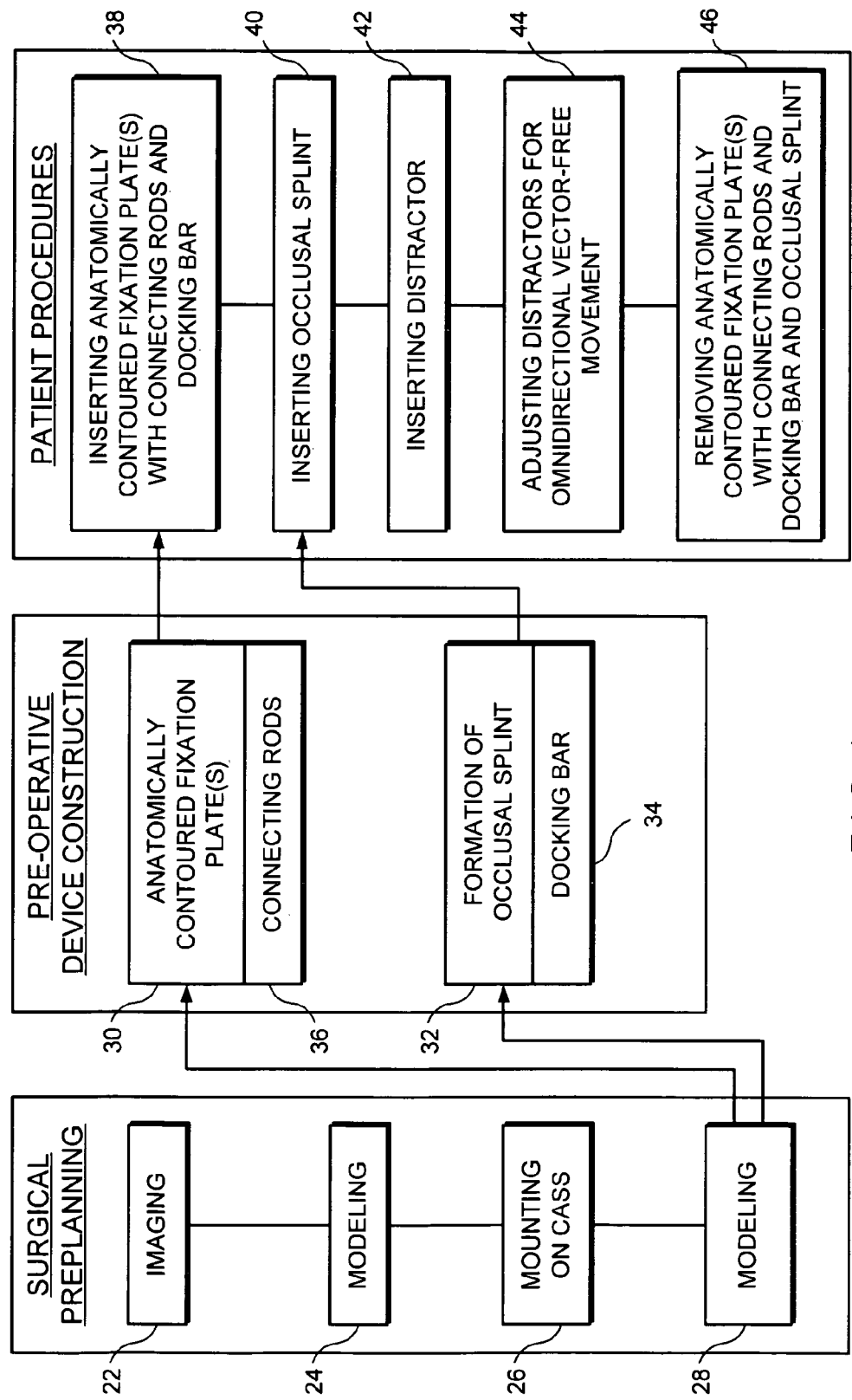
FIG. 1 is a schematic diagram of the new system of orthopedic surgery for which the craniofacial anatomic surgical simulator is designed.

Referring to the schematic diagram of the system FIG. 1, a general overview of the new system of orthopedic surgery is now provided. Three principal divisions are apparent, namely, (1) surgical preplanning; (2) pre-operative device construction; and, (3) patient procedures.

Upon initializing the process, an IMAGING 22 of the patient is first undertaken. The IMAGING 22 step may obtain digitized data from scans of magnetic resonance imaging (MRI), X-ray, computed tomography (CT), ultrasound, laser interferometry or position emission technique (PET). From the collected data, accurate anatomic information as to the bone formation and bone malformation is available.

A medical model, preferably stereolithographic, is formed using MODELING 24 techniques presently extant. Typical of the available modeling techniques are those described in a Christensen, U.S. Patent Application Publication 2005/0133955 for custom prosthesis development. In preparation for the mounting of the model on the craniofacial anatomic surgical simulator which follows, the segments of the stereolithographic model are carefully evaluated.

The inventor's craniofacial anatomic surgical simulator, described in detail herebelow, is now used to mount the parts of the stereolithographic model in the pre-operative positions thereof. The MOUNTING ON CASS 26 process is key to the extreme accuracy of the omnidirectional distraction. The MOUNTING ON CASS 26 process provides the facility for accurately forming the docking bar and the surface mapping required for the anatomically contoured fixation plates and the process does so without the need for vector determination or vector guides.

The mounted stereolithographic medical model also provides, during surgical preplanning, for the SIMULATING 28 phase. Here any osteotomy required and the incisions for installing the custom-fitted fixation plates are preplanned. Upon receipt of the customized distraction device from the laboratory, the casting is fitted to the model and, with the docking bar in place, the day-to-day distraction movement and adjustment is planned.

Pre-Operative Device Construction

Figure 4:
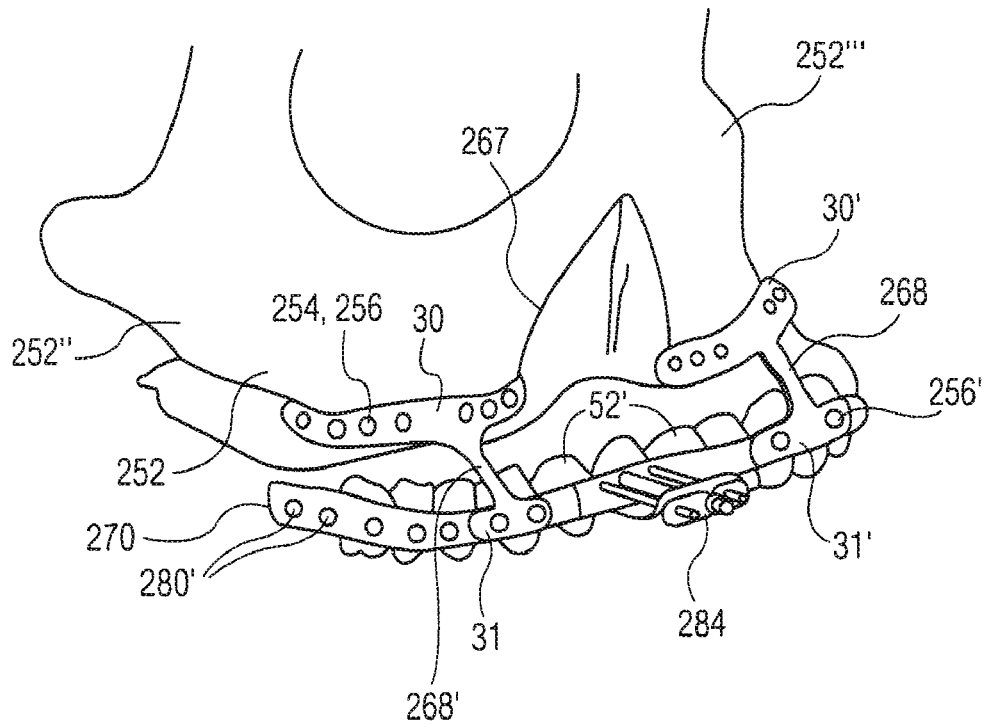
FIG. 4 is a perspective view of the intra-oral device of this invention for maxillofacial omnidirectional distraction osteogenesis.
Figure 5:
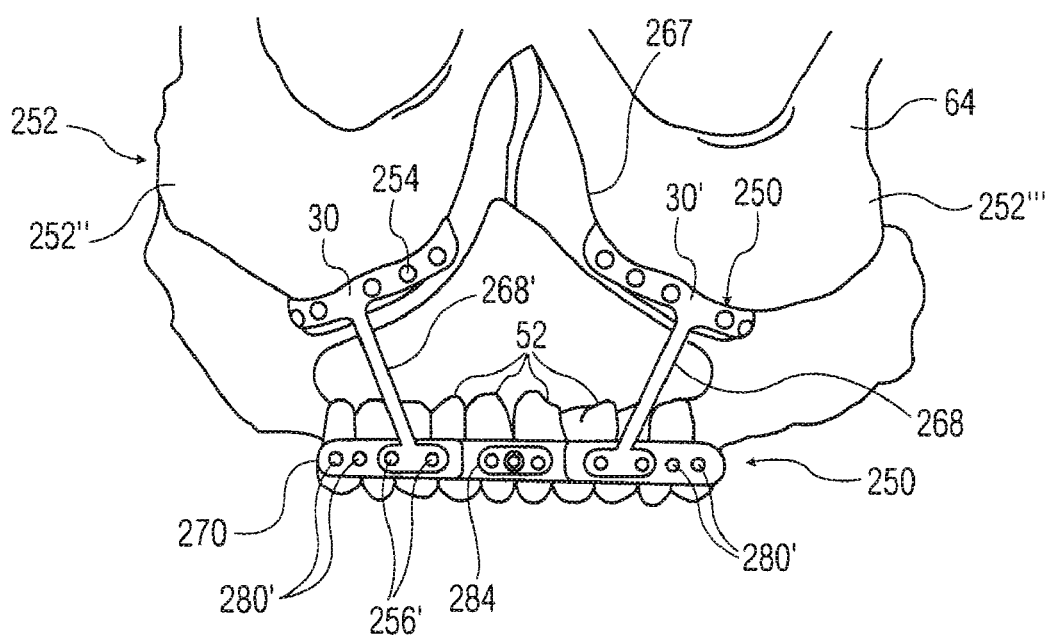
FIG. 5 is a front elevational view of FIG. 4.

Using omnidirectional distraction osteogenesis as an example, the surgeon, either alone or with the support team, forms a wax model for lost-wax casting of ANATOMICALLY CONTOURED FIXATION PLATES. (See FIGS. 4, 5, 6A, 6B, for an embodiment of exemplary plates 30, 30'.) In the example described below, the medical model, being an accurate representation of the cranial skeletal structure, custom fits the ANATOMICALLY CONTOURED FIXATION PLATES (plates 30, 30', FIGS. 4 and 5) to the malar bone 252 left segment 252" and right segment 252''' so as to follow the surface map of the bone contours at the site of installation. In this manner, the device is pre-operatively precision fitted to the patient and, unlike some prior art intra-oral devices, does not require bending at the time of installation. Besides the preciseness of custom-fitting and the removal of the bending requirement, the ANATOMICALLY CONTOURED FIXATION PLATES (plates 30,30') are devices which facilitate establishment of a rigid skeletal connection. These PLATES 30, 30' utilize anatomic undercuts (undercuts 264, 269, FIG. 9A) supplemented by bone screws (screws 256, FIG. 4).

Again using omnidirectional distraction osteogenesis as an example, the surgeon either alone or with the support team, places all the segments of the stereolithographic model in the post-operative position and forms an OCCLUSAL SPLINT/DOCKING BAR ARMATURE 32 assembly. A standard occlusal splint is modified by adding a convex peripheral docking surface which becomes the armature for constructing the docking bar, see infra. With the segments of the model assembled on the CASS in the final position to be attained, the steps of: (1) the preforming of the DOCKING BAR 34; (2) designing and forming of the CONNECTING RODS 36; and, (3) selecting the distractor mounting position complete the pre-operative device construction phase. These devices enable the surgical procedure in which full distraction in all directions becomes feasible.

Patient Procedures

Referring again to FIG. 1, the operative steps are now described. First, the step of inserting the devices fabricated pre-operatively is completed. The INSERTING ANATOMICALLY CONTOURED FIXATION PLATE(S) WITH CONNECTING RODS AND DOCKING BAR 28 is accomplished with the ends of the fixation plates anchoring the plates by wrapping around and undercutting the bones at the installation sites. The occlusal splint upon which the docking bar 34 was formed is inserted at INSERTING OCCLUSAL SPLINT 40.

With this accomplished, a distractor, such as a Dynaform distractor (as manufactured by Stryker Leibinger BmbH & Co., Freiburg, Germany) is employed, and emplaced on the docking bar at INSTALLING DISTRACTOR 42.

With the device installation completed, what remains is ADJUSTING DISTRACTORS FOR OMNIDIRECTIONAL VECTOR-FREE MOVEMENT 44 and REMOVING ANATOMICALLY CONTOURED FIXATION PLATE (S) WITH CONNECTING RODS AND DOCKING BAR AND OCCLUSAL SPLINT 46.

Craniofacial Anatomic Surgical Simulator

Figure 2:
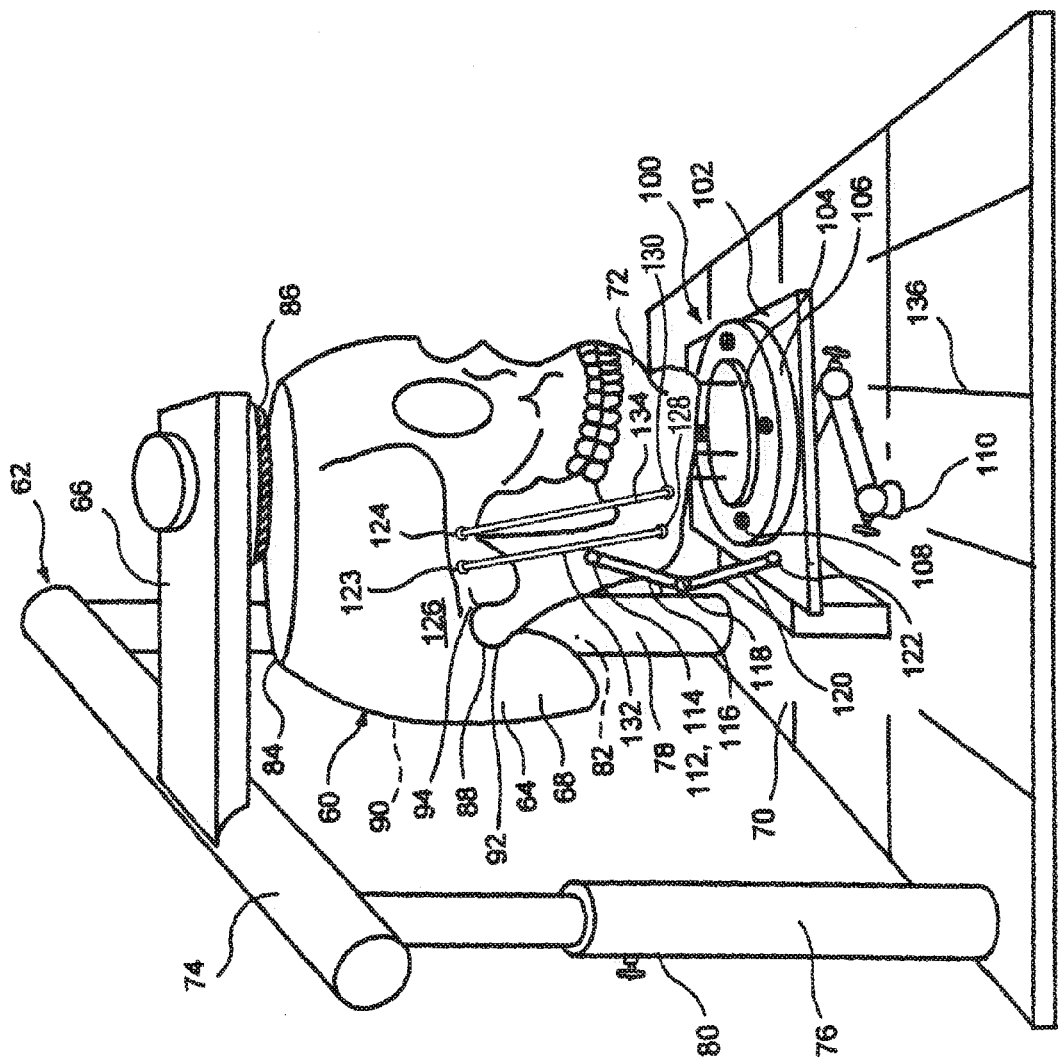
FIG. 2 is a perspective view of the first embodiment of the craniofacial anatomic surgical simulator of this invention having a uniquely positionable mandibular mounting arrangement.
Figure 2:
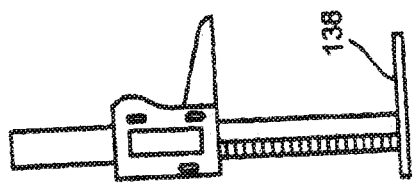

Referring now to FIG. 2, the craniofacial anatomic surgical simulator (CASS) is now described. The CASS is referred to generally by the reference designator 60 and provides a framework 62 for accommodating the stereolithographic model 64. The framework 62 is constructed with an upper mounting plate 66 for attaching the craniomaxillary portion 68 of the stereolithographic model 64 and a base mounting plate 70 for attaching the mandibular portion 72 of the stereolithographic model 64.

The framework 62 of the CASS 60 further comprises a crossbar or strut 74 to which the upper mounting plate 66 is connected. While in the present embodiment the strut 74 upper mounting plate 66 is fixed, it is within the contemplation of the present invention that this connection could swivel for adjustment thereof. The framework 62 of the CASS 60 further comprises adjustable posts or retaining elements 80 and 82 that maintain the upper mounting plate 66 at the selected elevation.

The medical model 64 consisting of the craniomaxillary portion 68 and the mandible or mandibular portion 72 is adapted for mounting on the CASS 60. The craniomaxillary portion 68 is modified for the purpose of the above-described surgery by having the uppermost cranial portion removed and replaced by a cranial attachment plate 84 which is mounted to the upper mounting plate 70 by an adhesive layer 86.

An artificial temporomandibular joint (TMJ) 88 and 90 is constructed to attach the mandible 72 between the base 70 and the craniomaxillary portion 68. As the stereolithographic model 64 does not represent the soft tissue component of the TMJ 88 and 90, the opening in the glenoid fossae 92 is filled with soft resilient dental liner or reline 94 (such as COE-SOFT Resilient Dental Liner manufactured by GC America, Inc., Alsip, Ill. 60803 or equivalent). This enables the mandible 72 to rotate during simulated surgery in an accurate manner.

The mandible 72 is also attached through a mandibular mounting mechanism 100 to the base mounting plate 70. The mounting mechanism 100 is constructed with a mandibular base plate 102 and intermediate plates 104 and 106. In the embodiment shown, plate 106 is attached to mandibular base plate 102 with three positioning screws 108 enabling the removal and remounting of the mandible 72 without losing the original location or orientation.

The mandibular mounting mechanism 100 is attached to the base 70 of the CASS 60 with two posts (not shown) and three universal movement lock joints 110. During simulated surgery, this mounting arrangement enables the movement of the mandible 72 vis-á-vis the craniomaxillary portion into the desired post-operative position.

When the CASS 60 is used to simulate mandibular ramus surgery, it is necessary to configure the device so that the proximal segment of the mandibular ramus is fixed. To accomplish this, a ramus pin 112 is disposed on both sides of the stereolith model 64 and a ramus pin lock joint 114, similar to lock joint 110, is secured thereto. Depending from lock joint 114 is upper guide rod 116, which, in turn, is secured to intermediate lock joint 118 and to lower guide rod 120. The lower guide rod 120 is secured to mandibular base plate 102 through base plate lock joint 122. With this structure in place, the mandible 72 relationship to the craniomaxillary portion 68 is adjusted by re-orienting lock joint 110. This is accomplished by unlocking the previously described lock joints sliding and rotating the segments to the desired position and locking the joints.

Optionally, at an angle mimicking the massateric sling, on both sides of the stereolithographic model 64, upper pegs 122 and 124 are placed in the zygomatic arch 126 and lower pegs 128 and 130 are placed in the mandible 72 with elastics 132 and 134 therebetween.

In operation the CASS 60 fulfills numerous pre-surgical functions. Specific to craniofacial surgery, the CASS 60, because of its extreme accuracy, facilitates the collection of cephalometric data. This is aided when a grid 136 is provided on base 102 for use in positioning measuring instruments.

Figure 3:
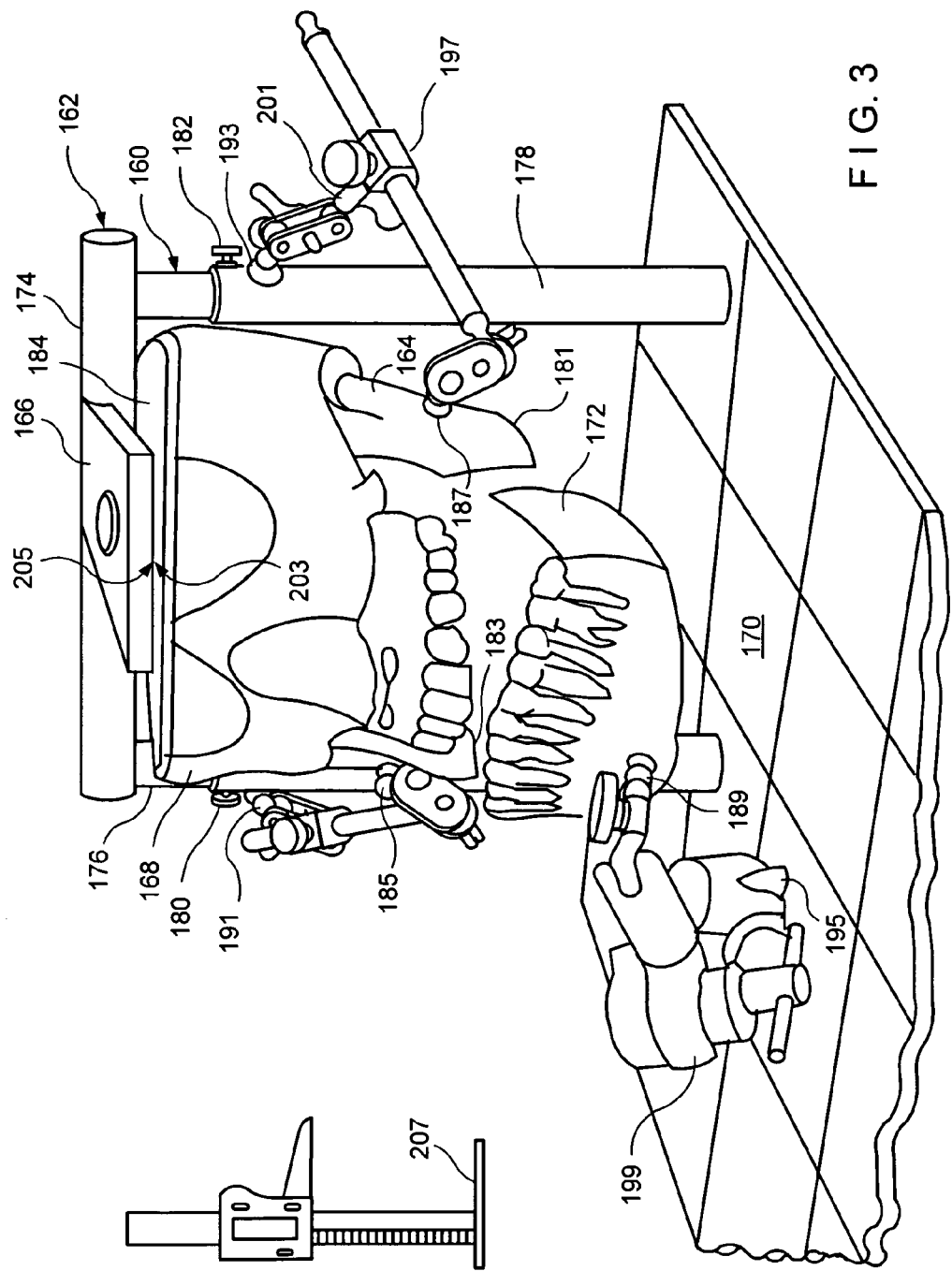
FIG. 3 is a perspective view of the second embodiment of the craniofacial anatomic surgical simulator of this invention utilizing transfer assemblies to hold segments of the stereolithographic model.

Referring now to FIG. 3, a second embodiment of the craniofacial anatomic surgical simulator (CASS) is shown and is now described. The CASS device is referred to generally by the reference designator 160. In this embodiment, similar parts to those of the first embodiment are referred to by reference designators 100 units higher than a similar part in the first embodiment.

The CASS device 160 provides a framework 162 for accommodating the stereolithographic model 164. The framework 162 is constructed with an upper mounting plate or extension arm 166. Optionally, the mounting plate 166 is constructed to include a universal swivel joint (not shown) for freely adjusting the same. The upper mounting plate 166 attaches the craniomaxillary portion 168 of the stereolithographic model 164. The framework 162 further includes a base mounting plate 170 for attaching the mandibular portion or mandible 172 of the stereolithographic model 164.

The framework 162 of the CASS 160 further comprises a crossbar or strut 174 to which the upper mounting plate 166 is connected. Adjustable posts 176 and 178 are held by retaining elements 180 and 182 to maintain upper mounting plate 166 at the selected elevation.

As previously mentioned, the stereolithographic model 164 consists of two basic parts, namely, the craniomaxillary portion 168 and mandible 172 is modified slightly differently from that of the first embodiment. Here, at each ramus segment 181 and 183, corresponding male attachment node or ramus connector 185 and 187 is emplaced. Similarly an attachment node or mandible connector 189 is emplaced on mandible 172. For easy management of the stereolithographic model 164, the framework 162 is constructed with a male attachment node or column connector 191 and 193 on each adjustable post 176 and 178, respectively, and at least one base connector 195 on base 170. Between ramus connector 185 and column connector 191, a manipulator or transfer device 197 (such as Kronus Helping Hands Model HD23, Catalog #64-2991, Radio Shack Corporation, Fort Worth, Tex. 76102 or equivalent) holds the ramus segment 181 (which has been separated from mandible 172). The stereolithographic model 164 can optionally be supplied with additional attachment nodes 189 for positioning other parts of the anatomy.

As shown in FIG. 3, a manipulator or transfer device 199 (such as Axiomatic Transfer Fork Assembly Model 050-155 of SAM—Präzisionstechnik Gmble, Gauting, Germany or equivalent) holds the mandibular segment 172 between base connector 195 and mandibular connector 189. Completing the mounting arrangement for the model 164, the ramus segment 183 in a manner analogous to segment 181, is held by a transfer device 201 between ramus connector 187 and column connector 193.

The stereolithographic model 164 is truncated by having the uppermost cranial portion removed and replace by a cranial mounting plate 184. In this embodiment the midlines of the cranial mounting plate 184 and the upper mounting plate 166 form a reference means with, for example, the midline 203 of cranial mounting plate 184 being raised and midline 205 of upper mounting plate 166 being indented. Thus, upon mounting, midline 203 interengages with midline 205 resulting in the positive indexing of stereolithographic model 164 on framework 162.

Maxillofacial Distraction Device

As described hereinabove, the stereolithographic model 64 is utilized to design and prepare castings of the ANATOMICALLY CONTOURED FIXATION PLATES 30. After a review of the stereolithographic model 64, the surgeon is able to design the ANATOMICALLY CONTOURED FIXATION PLATES 30 for the most reliable location of the bone screws. By preparing molded-to-patient, custom fit fixation plates, the installation thereof is simplified as the bending to fit of the presently extant plates or cloverleaf fittings is eliminated and overall operating time is reduced.

FIGS. 4-9B illustrate the craniofacial maxillary intra-oral distraction device 250 mounted on the stereolithographic model 64 showing the relationship among the major components of the device 250. The distraction device 250, FIGS. 4, 5, 6A, 6B, is used to distract the maxillary bone 50 via two maxilla bone segments 50' and 50", FIG. 14. These segments are fused to ether to form the single maxilla bone 50 of the upper jaw. The upper teeth 52 are attached to and depend from the maxillary bone 50. The device 250 comprises two contoured elongated fixation plates 30, 30', connecting rods 268, 268' corresponding to the respective fixation plates, attachment members 31, 31' attached to and corresponding to a respective end of the rods opposite the plates 30,30', a docking bar 270 to which the members are attached and a distractor 284 attached to the docking bar. The occlusal splint 276 (FIGS. 6A, 6B, not shown in FIGS. 4 and 5) is associated with a given patient's dentition and the docking bar, and is wired to the docking bar 270, to the distractor 284 and to the orthodontic appliance attached to the upper teeth 52. The distractor 284 distracts the maxilla bone via the splint 276. It should be understood that the drawings are not to scale and the shape and dimensions of the splint are schematic for purposes of illustration. The fixation plates 30, 30' are each attached to the respective corresponding malar bone 252 segments 252" and 252'" through bone-screw apertures 254 with bone screws 256, FIG. 4. The bone-screw apertures 254 are positioned all along the contoured fixation plates 30, 30', so that, from a review of the stereolithographic model 64, the surgeon is able to select the most reliable locations for bone screws 256 of the fixation plates 30, 30'. The fixation plates 30, 30' are positions relative to the undercuts of the maxilla bone 50 such that when the connecting rods 268, 268' are secondarily connected to the docking bar, the fixation plates become rigidly locked in place relative to the undercuts. It should be understood by one of ordinary skill that the fixation plates are removed from their rigid or secured position as desired by the surgeon at the completion of the distraction procedure.

Figures 9A, 9B:
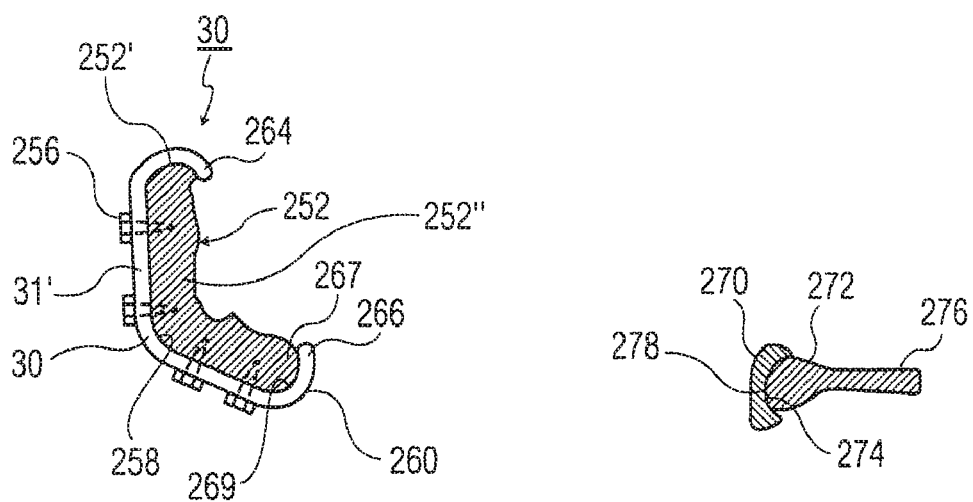

The cross-sectional view of FIG. 9A, which is representative, shows the contoured fixation plate 30 interior surface 258, which is configured to mate with the correspondingly contoured exterior surface 260 of the segment 252" of the malar bone 252. Upon installation, the "hills" and "valleys" of interior surface 258 fit into and mate with the interstices of the malar bone 252. In addition to the mating surfaces, the contoured fixation plate 30 wraps around the posterior edge 252' of the malar bone 252, undercutting the edge 252', with a malar hook 264, which further anchors this end portion of the distraction device 250. This posteriorly provided extension of the contoured fixation plates 30, 30' is also repeated in the anterior extension wherein a nasal-bone hook 266, FIG. 9A, wraps around the piriform rim 267 for anchoring the other end of the contoured fixation plates 30, 30'. Therefore, both hooks 264, 266 and the bone screws secure the contoured fixation plates 30, 30' to the respective malar bones, the fixation plates being stabilized by the bone screws.

Figure 6A:
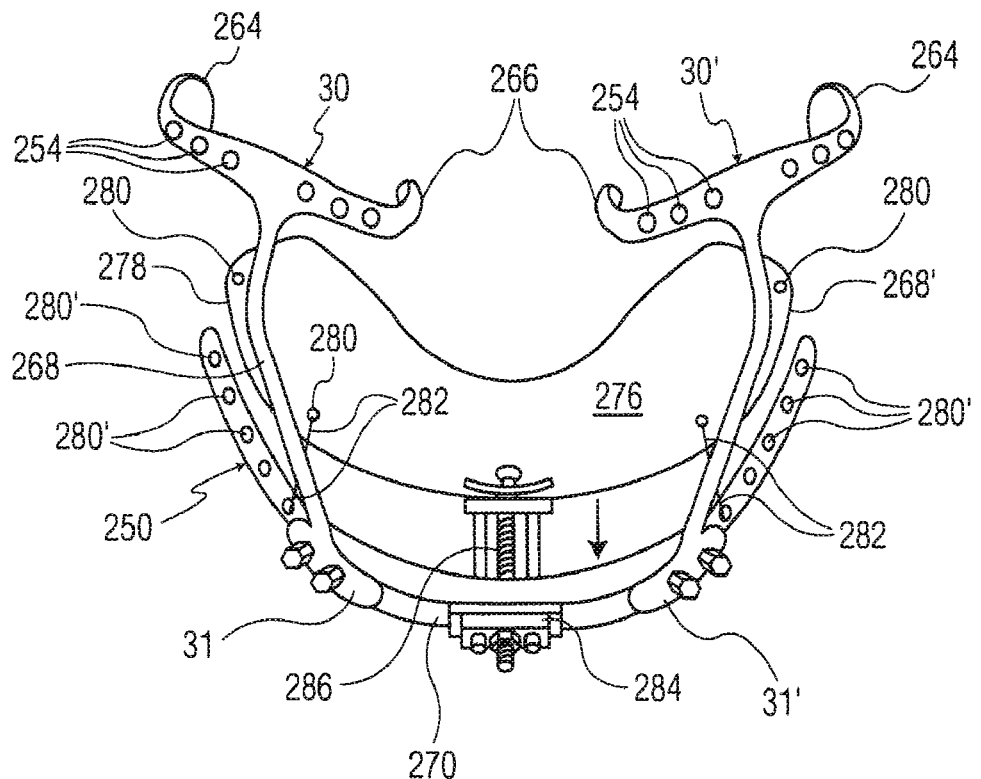
FIG. 6A is a top plan view of the anatomically contoured fixation plates, connecting rods, docking bar and occlusal splint shown with the docking bar and occlusal splint separated in the prior to distraction position.
Figure 6B:
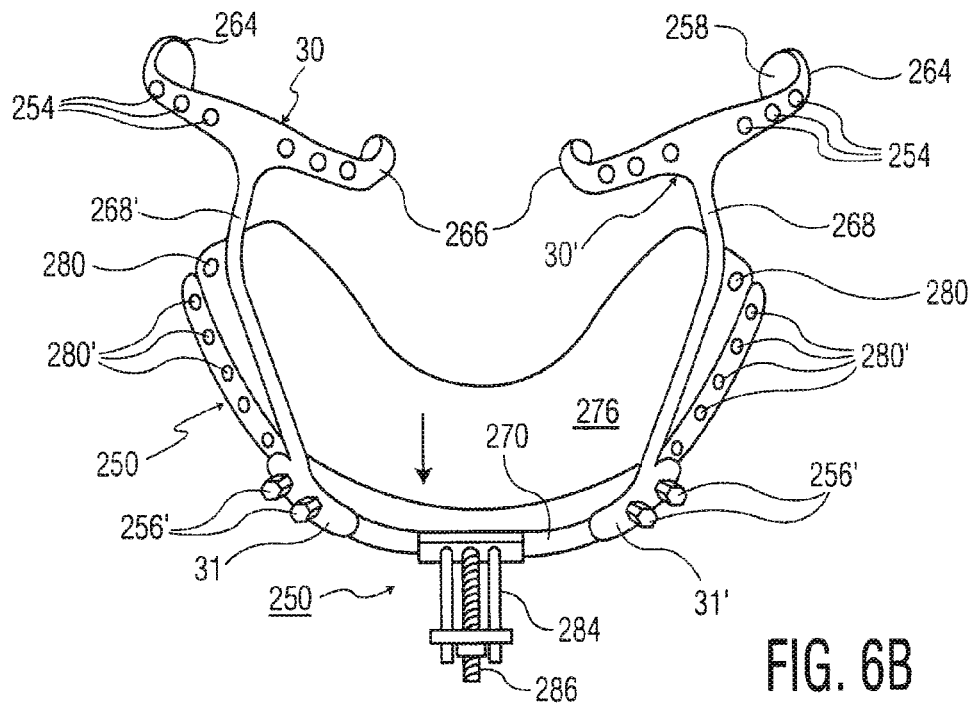
FIG. 6B is a top plan view of the anatomically contoured fixation plates, connecting rods, docking bar and occlusal splint shown with the docking bar and occlusal splint in the after distraction position.
Figure 7:
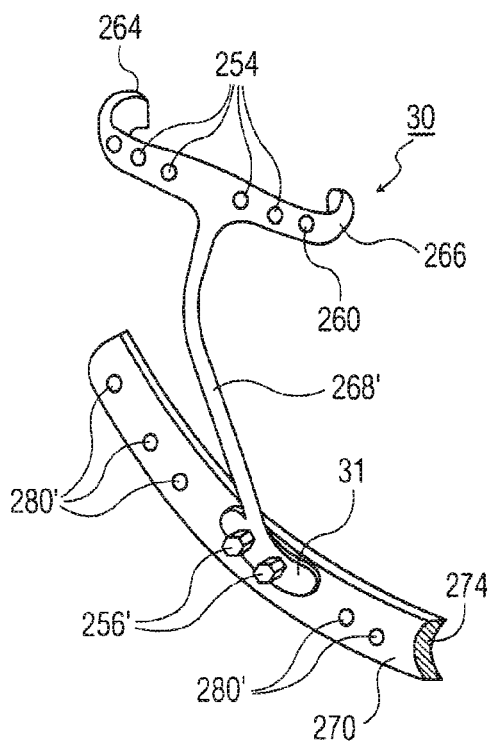
FIG. 7 is a front view of the anatomically contoured fixation plate, connecting rod and a portion of the docking bar of FIG. 6.
Figure 8:
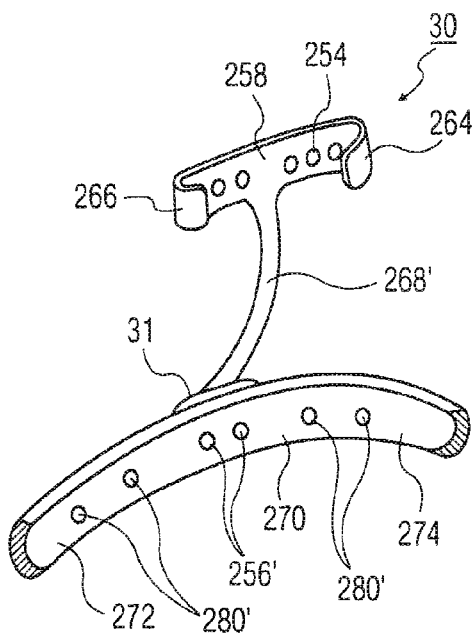
FIG. 8 is a rear view of FIG. 7 showing the contoured surface.
Figure 10:
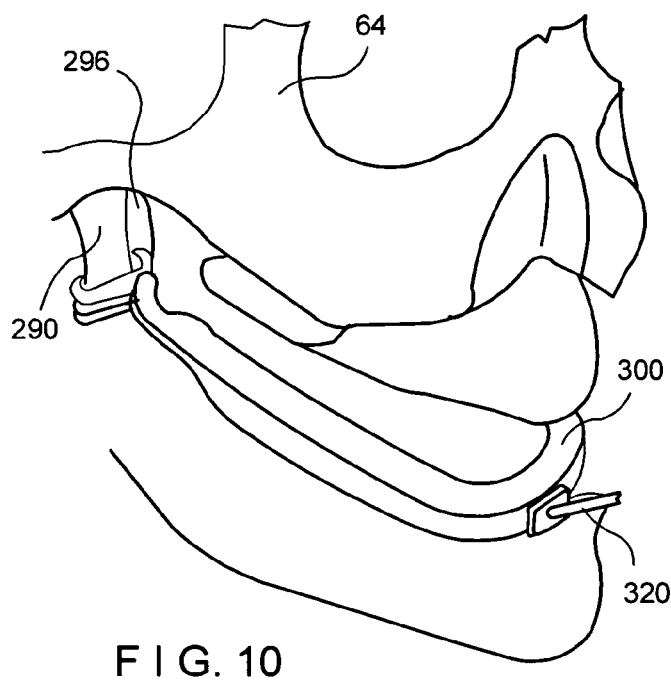
Figure 11:
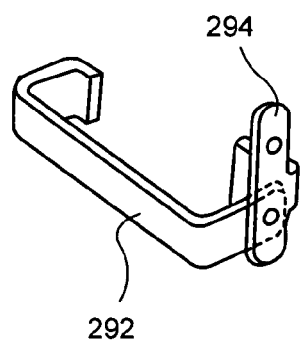
FIG. 11 is a perspective view of the ramus band assembly.
Figure 12:
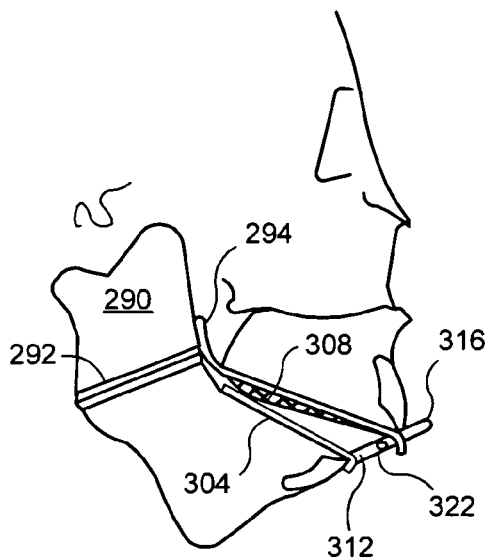
FIG. 12 is a cross-sectional view of the intra-oral device of FIG. 10 shown in the pre-operative position.
Figure 13:
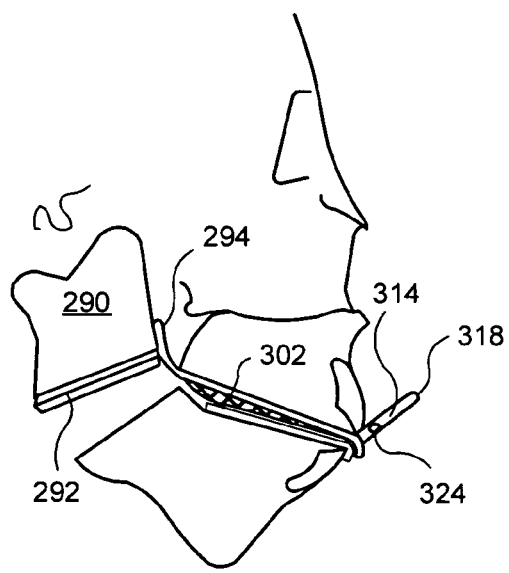
FIG. 13 is a cross-sectional view of the intra-oral device of FIG. 10 shown in the post-operative position.

In this embodiment, the contoured fixation plates 30, 30', with the bone hooks 264 (the malar anatomic retention contour) and 266 (the nasal anatomic retention contour), and the bone-screw apertures 254 are modeled in wax at the stereolithographic model 64 together with the one piece connecting rods 268, 268', illustrated in FIGS. 6A, 6B. The connecting rods 268, 268', attach docking bar 270 in a rigid manner to the contoured fixation plates 30, 30'. The attachment (which is in the area of the cuspid tooth) is at a critical angle and is maintained as close to horizontal as possible so that the distraction forces are transmitted substantially axially in the rods 268, 268' toward the contoured fixation plates 30, 30'. As a result, these forces are approximately normal to the respective fixation plates 30, 30'. These axial forces enhance the attachment of the contoured fixation plates 30, 30' to the mating bones in that they are applied to the fixation plates in a direction to force the plates against the malar bone. Thus, the distraction forces are distributed along the docking bar 270 and to the contoured fixation plates 30, 30' in a manner that minimizes dislodging forces on the fixation plates and rotational forces on the maxillary segments 50', 50", FIG. 14. The connecting rods 268, 268' are positioned, upon installation, to be disposed as close to the height of the buccal fold and as close to the maxilla as soft tissue closure permits.

While the contoured fixation plates 30, 30', and the corresponding connecting rods 268, 268', are respectively cast as a single unit from a wax model formed by a "hands on" session at the stereolithographic model 64, it is within the contemplation of this invention that the device comprising contoured fixation plates 30, 30', connecting rods 268, 268' and attachment members 31, 31' is formable through virtual imaging and advanced CAD/CAM techniques known in the digital modeling art. Also, even though the present configuration ensures rigidity by the unitary structure of the contoured fixation plates 30, 30', and the connecting rods 268, 268', it is contemplated as an alternate embodiment that the connecting rods 268, 268', are is constructed to be demountable from the respective contoured fixation plates 30, 30' (not shown). Further, the use of demountable connecting rods 268, 268' provide an option in post-operative care by permitting the surgeon to easily remove the appliance and leave the installed plates in situ.

Figure 14:
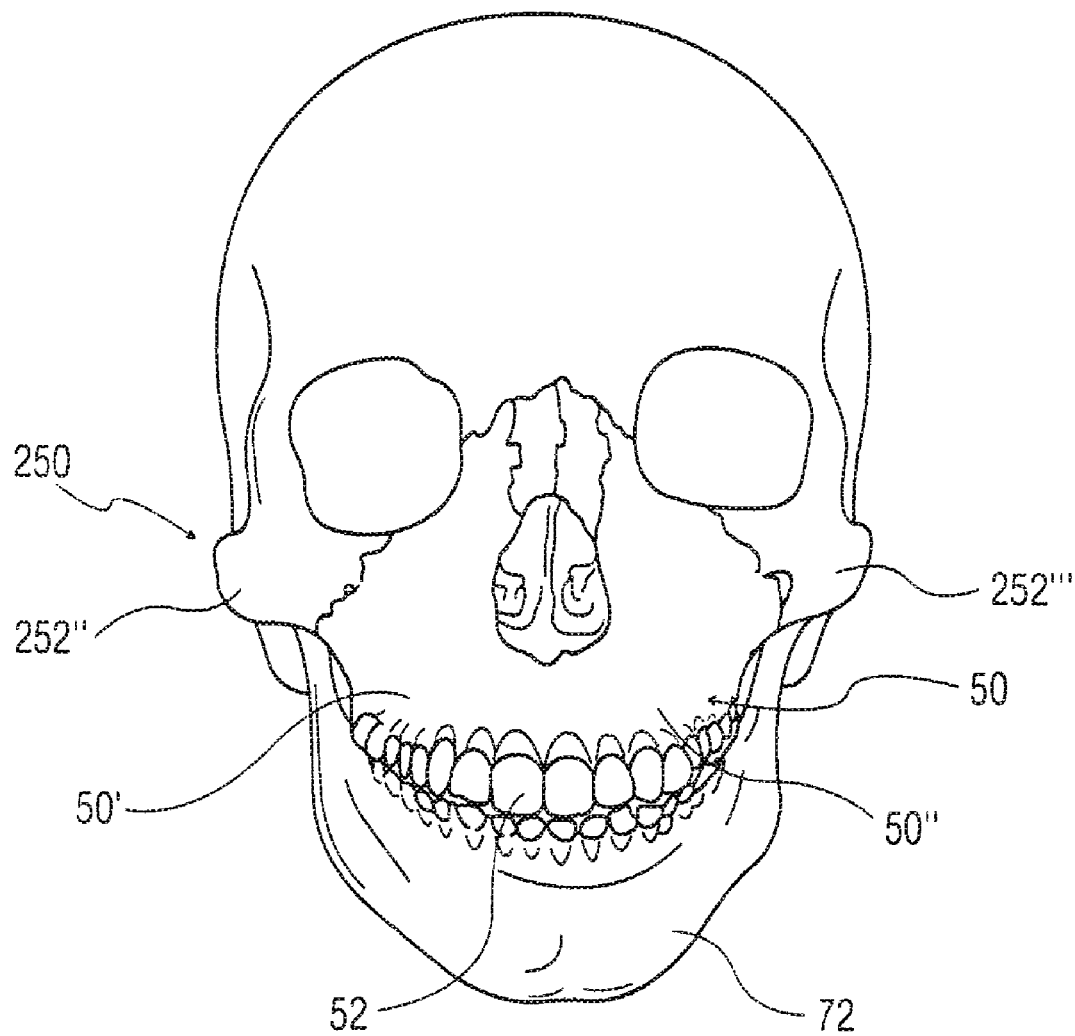
FIG. 14 is a front elevation view of a skull shown in the malar and maxilla bones.

The interior face 272 of docking bar 270 has a peripheral groove 274 therewithin (FIGS. 7, 8 and 9B), for establishing the endpoint of the total distraction of the maxillary bone 50 segments 50', 50", FIG. 14, upon abutment therewith by the occlusal splint 276 during the distraction. With the stereolithographic model 64 being used to simulate the surgery, the craniofacial components are placed in the post-operative positions. The occlusal positioning splint 276 is then molded from acrylic material to the patient's upper dentition. The splint 276 is articulated to the patient's final desired distraction position by the distraction as determined by the position of the groove 274 (FIG. 9B) of the docking bar 270 that mates with the splint 276. A bead or convex edge 278, FIG. 9B, is fashioned peripherally about the exterior of the splint 276 and is designed to mate with and be guided into peripheral groove 274 of docking bar 270. The occlusal splint 276 is wired to orthodontic appliances affixed to the patient's upper teeth 52, FIGS. 4, 5, 6A and 6B. Wires 282 coupling the splint to the docking bar 270 serve to guide the splint 276 toward the distraction device 284 and docking bar 270 during the distraction. The wires and splint are not shown in FIGS. 4 and 5. The splint 276 is not to scale and only shown schematically for illustration, and is shown without the wires to the teeth 52' in FIGS. 6A, 6B. The wires 282, FIG. 6A, their corresponding holes 280 in the splint 276 and holes 280' in the docking bar 270 are provided for distraction guiding the splint for docking fixation to the dock 270 during the distraction which pulls the splint and the maxilla bone toward the docking bar. Wires, such as wires 282, (and those not shown), affix the splint 276 to the distractor 284 and to the docking bar 270. Adjustment of one or more of the wires during distraction provides omnidirectional control of the trajectory and docking of the splint as it is distracted into abutment with the groove 274 of the docking bar 270, FIG. 9B. The splint forms a docking transporter.

In the appropriate position to ensure accurate docking, screw-type distractor 284 is mounted medial the docking bar 270 with the wires 282, FIG. 6A, extending therefrom into and through the holes 280 in splint 276. The intra-oral distraction device 250, upon installation, is operated by the screw 286 of the distractor 284 that advances the maxillary bone 50, FIG. 14, under distraction towards the docking bar 270, FIGS. 6A, 6B, via the motion of the splint 276. The motion of the splint is guided by the wires 282 (as periodically adjusted during the distraction) until the splint is seated in the endpoint docking groove 274 (FIG. 9B) of the docking bar 270. The splint 276 is guided into the groove in the desired direction by the wires 282. In such a distraction process, the bone is severed, and the separated bone pieces are moved apart gradually by the distraction. As the pieces are moved apart, new bone is allowed to grow in the gap. The separation of the bone pieces is continued by further distraction until the desired bone growth length is reached as determined by the endpoint of the groove 274 in the docking bar 270. Wires 282 serve to stabilize the maxillary bone to reduce disruptcy to the healing tissue during the distraction procedure.

The splint 276 and the maxillary bone 50 segments 50′, 50″ attached thereto via the upper jaw dentition are drawn toward the docking bar 270 groove 274 concavity by the adjustment of the screw 286, FIGS. 6A, 6B. Any slight misalignment is corrected by periodic adjustment of the docking/fixation wires 282 during the distraction so that the post-operative position determined at the simulation surgery stage is replicated during the actual operation. With the entire convex edge 278 of splint 276, FIG. 9B, nesting within and abutting against the concave surface of groove 274 of docking bar 270, FIGS. 8 and 9B, the splint 270 thus has been displaced via the wires 282, FIG. 6A, relative to the docking bar in an omnidirectional splint displacement. This displacement is determined by the wiring and distraction and is independent of a particular force vector. The wiring thus controls the trajectory and docking of the splint 276 acting as a maxillary bone docking transporter. When the docking is achieved, if the distractor 284 mounting may be disassembled, the surgeon may remove the distractor 284 for the patient's comfort during the consolidation period. The docking/fixation wires 282 are now tightened to secure the splint to the docking bar. It is within the contemplation of this invention that multiple distractors may be attached at the same time to the docking bar for maxillofacial distraction. Each distractor would simultaneously serve to translate on a separate trajectory a respective maxillary bone segment 50′, 50″, FIGS. 6A, 6B and 14, to which it is attached.

Mandibular Distraction Device

The extant intra-oral devices for mandibular distraction osteogenesis are compromised by the action thereof on the temporomandibular joint (TMJ), which actions deflect the condyle and dissipate the distraction forces. Referring now to FIGS. 10-13, the mandibular distractor hereof overcomes the TMJ mobility by constructing an occlusal platform rigidly tied to the rami, which platform acts as a fixed base for distraction and directs the distraction forces to the mandibular body.

Working with the stereolithographic model 64 mounted on the CASS device 60, each ramus 290 has constructed therefor a hooked two-piece ramus band 292 and 294. The ramus band 292 and 294 is custom-fitted and modeled in wax in a manner similar to contoured distraction plate 30, supra. The ramus band assembly 292 and 294 extends about the ramus 290 with the inferior hook and band portion 292 being attached by the interlocking superior hook and securement portion 294 to the retromolar ascending ramus 296 area.

This banding arrangement of the rami serves as a mounting point for a horseshoe-shaped occlusal platform 300 which extends from ramus to ramus and provides the requisite mandibular segment stabilization during distraction osteogenesis. The underside 302 of the occlusal platform 300 provides the housing for a molded acrylic occlusal dock for the mandibular distraction. During the presurgical planning, the mandible of the stereolithographic model 64 is sectioned and positioned in the desired post-operative position. A mandibular occlusal splint 304 is fashioned on the model and an acrylic impression thereof is disposed on the underside of the occlusal platform 300 so that upon reaching the endpoint of the distraction, the mandibular occlusal splint 304 is fully nested in the occlusal dock 308 at the underside 302 of occlusal platform 300.

Attached to and on either side of the mandibular occlusal splint are guides 312 and 314 that accommodate guide rods 316 and 318 mounted on the occlusal platform 300. The guide rods are shaped and positioned in accordance with the trajectory of the mandibular segment. A distractor 320 is appropriately mounted on occlusal plate 300 and in accordance with the distraction osteogenesis program is periodically adjusted until the mandibular segment is translated from the pre- to postoperative position. Additionally guides 312 and 314 incorporate locking screws 322 and 324 to ensure rigidity of the mandibular segment between periodic adjustments. The locking screws 322 and 324 are released during adjustment and tightened thereafter.

The distractor 320 is optionally permanently installed to the occlusal platform 300 or demountably installed thereto. In this manner, with a demountable distractor 320, the patient may be more comfortable during post-operative consolidation period.

Because many varying different embodiments may be made within the scope of the inventive concept herein taught and because many modifications may be made in the embodiments herein detailed in accordance with the descriptive requirements of the law, it is to be understood that the details herein are to be interpreted as illustrative and not in a limiting sense.

What is claimed is:

1. An intra-oral distraction device for distraction osteogenesis of the maxillary bone, said intra-oral distraction device for attachment to and disposition upon an anchoring bone or bones each having a contoured surface and contoured edges, said intra-oral distraction device comprising:
a first fixation plate having an elongated body with an interior surface and an exterior surface, said interior surface being configured for anatomically mating with said contoured surface and for engaging with and about said contoured edges of said anchoring bone to secure the fixation plate to said anchoring bone;
a docking structure rigidly attached to the first fixation plate for receiving an occlusal splint coupled to the maxillary bone to be distracted; and
a distractor attached to said docking structure and coupled to the maxillary bone for distracting the maxilla bone of the patient relative to the anchoring bone the coupling of the docking structure and the distractor to the splint for providing omnidirectional control of said distraction.

2. The intra oral device of claim 1 wherein the anchoring bone comprises the malar bone having first and second segments, the device including a further fixation plate forming a pair of fixation plates with the first fixation plate, each fixation plate for attachment to a separate different one of said malar bone segments; and
an attachment arrangement including a pair of connecting rods, each rod of the pair being affixed to and corresponding to a different one of said fixation plates, the rods being arranged to extend outwardly and downwardly from the corresponding fixation plate;
the docking structure including a docking bar configured to be arrayed about the maxillary arch of the patient, said docking bar for rigid attachment to said connecting rods at the rod ends opposite said fixation plates, said docking bar having a concave interior groove for receiving the distraction splint.

3. The intra-oral device of claim 2 wherein said connecting rods are demountable from the docking bar.

4. The intra-oral device of claim 1 wherein the contoured edges comprise a first edge and a second edge, the docking structure including a connecting element for rigidly connecting said fixation plate to the distractor; a first hook formed in the fixation plate for extending about the first edge of said anchoring bone for further securing said fixation plate to the anchoring bone first edge; and second hook formed in the fixation plate for extending about the second edge of said anchoring bone for further anchoring, said fixation plate to the second edge.

5. The intra-oral device of claim 1 wherein said docking structure includes a docking bar having opposing ends and a concave groove, the distractor being attached to said docking bar medial the ends of the docking bar for movement of the maxillary bone during the distraction; and the occlusal splint being attached to the maxillary bone for engagement with the concave groove of said docking bar, said occlusal splint being connected by wires to the docking bar and coupled to the maxillary bone, said occlusal splint having a convex exterior rim, for being received within and mating with said docking bar concave groove, with full omnidirectional vector control of the trajectory and docking of the maxilla via the wires to thereby provide a maxilla docking transporter.

6. The intra-oral device of claim 1 further including an occlusal splint, wherein the docking structure includes a plurality of adjustable wires for coupling the splint to the docking bar and to the maxillary dentition to thereby provide the omnidirectional control of the splint during distraction.

7. An intra oral distraction device for maxillofacial distraction osteogenesis and for attachment to and disposition upon a malar bone of a patient, said malar bone having first and second segments each having a contoured surface, said intra-oral device comprising:

a pair of fixation plates each corresponding to and for attachment to a different one of said first and second malar bone segments, each fixation plate having an elongated body with an interior surface and an exterior surface, each said distraction fixation plate interior surface having a contour configured to anatomically mate with said contoured surface of said corresponding first and second segments of the malar bone;

a docking structure for coupling to the upper dentition of a patient including a docking bar and a distractor attached to the docking bar, the docking bar and distractor for receiving an occlusal splint coupled to the docking bar and to the upper dentition, the coupling of the distractor and docking bar to the occlusal splint for providing omnidirectional control of the positioning of the maxillary bone via the upper dentition; and an attachment arrangement for rigidly connecting said fixation plates to the docking structure;

whereby distraction osteogenesis is enabled with full omnidirectional vector control of the positioning of the maxilla bone.

8. The intra-oral device of claim 7 further including a connecting rod corresponding to and coupled to each said fixation plate, the rod extending outwardly and downwardly from each said corresponding fixation plate.

9. The intra-oral device of claim 8 wherein each said connecting rod is releasably secured to said docking structure to releasably lock said corresponding fixation plate in place.

10. The intra-oral device of claim 7 further including a connecting rod corresponding to and coupled to each said fixation plate, the rod extending outwardly and downwardly from each said fixation plate, said connecting rod being integral and one piece with each said corresponding fixation plate said docking bar being configured to be arrayed about the maxillary arch, said docking bar for rigid attachment to each said connecting rods at a the respective end thereof remote from said corresponding fixation plate, said docking bar having a groove for establishing a predetermined distraction endpoint;

a distractor mounted on said docking bar medial the ends of the docking bar arranged for providing movement of the occlusal splint set forth below during the distraction; and an occlusal splint for coupling to the maxillary dentition and for being received within said docking bar groove, said occlusal splint having a convex exterior rim, whereby, in response to movement imparted the distraction, said occlusal splint convex exterior rim being received by said docking bar groove and being so attached to the docking bar and to the maxillary dentition to provide omnidirectional vector control relative to the docking bar during the distraction.

11. The intra-oral device in claim 10 wherein said docking bar groove is concave groove.

12. The intra-oral device of in claim 7 having two or more bone-screw apertures through each said fixation plates for receiving respective bone screws therethrough to secure the fixation plates to said malar bone segments.

13. The intra-oral device of in claim 7 wherein the contours of each said fixation plates are arranged to mount interstitially into the contours of the malar bone segments.

14. The intra-oral device of claim 7 wherein each said fixation plate includes a malar hook configured to extend about the posterior/inferior edge of said malar bone to further anchor each said fixation plate to a malar bone segment.

15. The intra-oral device of claim 7 wherein each said fixation plate includes a nasal hook configured to extend about the anterior edge of said malar bone segment at the piriform rim to anchor each said fixation plate to a malar bone segment.

16. The intra-oral device in claim 7 wherein further including a connecting rod corresponding to and coupled to each said fixation plate, the rod extending outwardly and downwardly from each said corresponding fixation plate, said connecting rods being integral and one piece with each of the corresponding fixation plates.

17. The intra-oral device of claim 7 wherein the docking structure includes a plurality of adjustable wires for coupling the splint to the docking bar and to the maxillary dentition to thereby provide the omnidirectional control of the splint during distraction.

* * * * *